United States Patent
Buchi

[11] 3,981,920
[45] Sept. 21, 1976

[54] METHOD FOR PREPARING CYCLOPENTENONE DERIVATIVES

[75] Inventor: George Hermann Buchi, Cambridge, Mass.

[73] Assignee: Firmenich S.A., Geneva, Switzerland

[22] Filed: May, 1968

[21] Appl. No.: 728,050

[30] Foreign Priority Application Data

Mar. 3, 1964 Switzerland ..............................2638/64

Related U.S. Application Data

[63] Continuation of Ser. No. 436,680, March 2, 1965, abandoned.

[52] U.S. Cl. ....................... 260/593 R; 260/346.1 R
[51] Int. Cl.$^2$ ......................................... C07C 49/12
[58] Field of Search ............... 260/593, 586, 593 R, 260/346.1

[56] References Cited
OTHER PUBLICATIONS

Stork et al. J. Am. Chem. Soc. vol. 86, pp. 936–937 (1964).
Beilstein's Handbuch der Organischen Chemie, vol. I, pp. 3161–3162 (1959).
Chemical Abstracts, vol. 50, 5569(b).
Gilman et al., J. Am. Chem. Soc. vol. 56, pp. 1123–27 (1934) *Gilman et al. III.
Morrison and Boyd, "Organic Chemistry" pp. 834, 837–838, and 840–841 (1959).
Gilman (I): Gilman et al., J. Am. Chem. Soc. vol. 61, 1939, pp. 109–112.
Gilman (II): Gilman et al., J. Am. Chem. Soc. vol. 62, 1940, pp. 1843–1846.
Berichte (I): Berichte, vol. 75, pp. 447–454 (1942).
Berichte(II): Berichte, vol. 75, pp. 460–468 (1942).

Dunlop, The Furans, ACS Monograph Series 1953, pp. 640–642.

*Primary Examiner*—Gerald A. Schwartz
*Attorney, Agent, or Firm*—Wenderoth, Lind & Ponack

[57] ABSTRACT

The invention provides a method for the preparation of 2-cyclopenten-1-one derivatives. The process involves metalating 2-methylfuran in the 5-position by an interchange reaction with an alkali metal-organic compound, condensing the resulting metal derivative of 2-methylfuran with a halide of the formula R—CH$_2$—X, wherein R represents an unsubstituted acyclic hydrocarbon radical which is free of triple bonds, comprises from 0 to 2 double bonds and contains from 3 to 5 carbon atoms and X represents a halogen, in order to form a 2,5-disubstituted furan of the formula

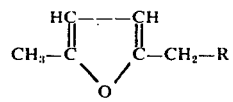

treating the disubstituted furan with an acidic agent to cause the opening of the furan ring and the formation of a dione of the formula

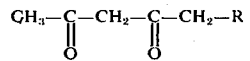

and cyclizing the dione by a treatment with alkali. The invention also provides certain novel 2-cyclopenten-1-one derivatives which are useful as fragrant ingredients in the manufacture of perfume compositions and which constitute valuable starting materials in the manufacture of other useful organic compounds.

8 Claims, No Drawings

METHOD FOR PREPARING CYCLOPENTENONE DERIVATIVES

This application is a continuation application of application Ser. No. 436,680, filed Mar. 2, 1965 now abandoned.

The present invention relates to a new method for preparing fragrant 2-cyclopenten-1-one derivatives part of which are new compounds. The invention also relates to the new 2-cyclopenten-1-one derivatives.

The cyclopentenone derivatives which can be obtained by the method of this invention have the following general formula

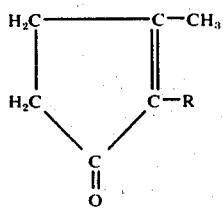

the meaning defined above and X represents a halogen, in order to form a 2,5-disubstituted furan of the formula

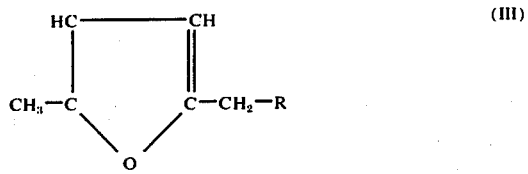

treating the disubstituted furan with an acidic agent to cause the opening of the furan ring and form a dione of the formula

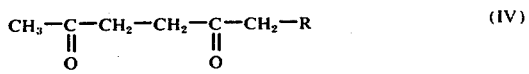

and cyclizing the dione by a treatment with alkali.

The method defined above can be illustrated by the following reaction scheme:

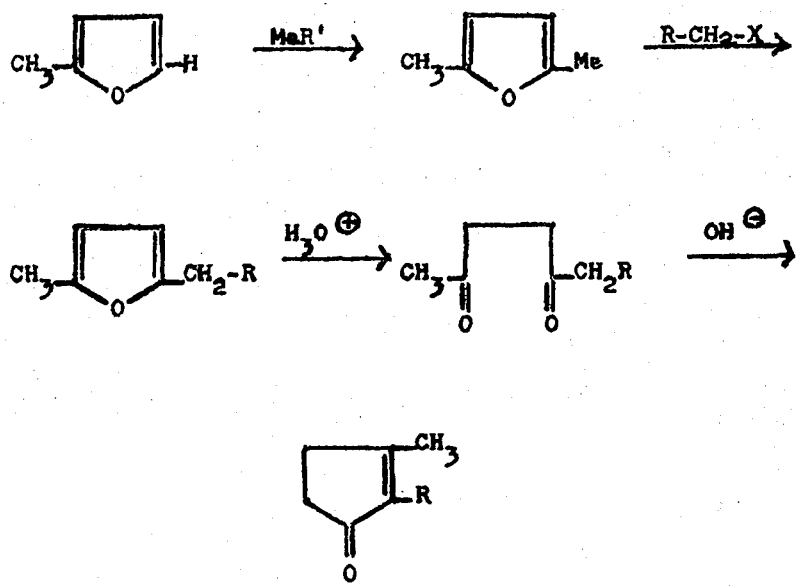

wherein R represents an unsubstituted acyclic hydrocarbon radical which is free of triple bonds, comprises from zero to two double bonds and contains from three to five carbon atoms.

The substituent R in formula I can be an unsubstituted straight-chained or branched alkyl having from three to five carbon atoms, an unsubstituted straight-chained or branched alkenyl having from three to five carbon atoms, or an unsubstituted alkadienyl having four or five carbon atoms. As examples of substituents represented by R there can be mentioned pentyl, 2-propenyl, 2-butenyl, 3-methyl-2-butenyl, 2-pentenyl, 3-pentenyl, 4-pentenyl and 2,4-pentadienyl.

The method of this invention comprises metalating 2-methylfuran in the 5-position by an interchange reaction with an alkali metal-organic compound, condensing the resulting metal derivative of 2-methylfuran with a halide of the formula R—CH$_2$—X (II), wherein R has Me = alkali metal
R' = organic radical
R = same meaning as in formula (I)
X = halogen 2-(cis-2-Pentenyl)-3-methyl-2-cyclopentenone (R = cis-2-pentenyl in formula I), more generally known under the name "cis-jasmone", is a particularly valuable odoriferous substance which is indispensable to the perfume industry. The classical method according to which jasmone was hitherto generally prepared consists in converting 3-hexenol into 3-hexenyl bromide, preparing 4-heptene carboxylic acid nitrile from the bromide by means of sodium cyanide, saponifying the nitrile with alkali to form 4-heptene carboxylic acid and converting the resulting acid into its chloride, condensing the acid chloride with the sodium derivative of ethyl acetoacetate, converting the resulting 4-heptenoyl-acetoacetate into methyl 4-heptenoyl-acetate by means of sodium methoxide, condensing the sodium derivative of this ester with bromoacetone, and cyclising the resulting α-(4-heptenoyl)-lacvulate by treatment with alkali to form jasmone [cf. Ber. 75, 460 and foll. (1942)]. This synthesis which comprises 8 steps is extremely time-consuming and involves high expenditure in terms of labour and equipment cost. Moreover, the crude cyclisation product must be subjected to complicated purification operations in order to obtain a reasonably pure jasmone. The yields of jasmone which can be obtained by this method are on average only about 14% of the theory based on 3-hexenyl bromide. Jasmone prepared according to the classical method is therefore an expensive product which cannot be used to the desired extent in the perfume industry.

It has furthermore been suggested [cf. Ber. 75, 460 and foll. (1942)] that jasmone be prepared by a method in which methylfurfurol is condensed with methyl propyl ketone, the obtained 2-methyl-5-(3-oxo-1-hexenyl-furan is reduced by means of sodium amalgam to 2-methyl-5-(3-oxo-1-hexyl)-furan, the latter is converted into 2-methyl-5-(3-hydroxy-hexyl)-furan by means of isopropanol and aluminium isopropoxide, the secondary alcohol is dehydrated to obtain 2-methyl-5-(1-hexenyl)-furan (mainly in the form of the trans-isomer), the furan derivative is treated with acid to open the furan ring and finally the resulting 8-undecen-2,5-dione is cyclised with alkali. This 6-step-method is complicated as well and gives only small yields of jasmone in the form of the trans-isomer which is less interesting for the perfume industry (about 3–4% of the theory, based on the methylfurfurol used). In particular, poor yields (about 7%) of 8-undecen-2,5-dione are obtained from 2-methyl-5-(1-hexenyl)-furan (cf. page 641, table 1, line 7, in "The Furans" by A. P. Dunlop and F. N. Peters, Reinhold Publishing Company, New York, 1953). This method has, therefore, never been of any practical value in the manufacture of jasmone.

The method of the invention constitutes a considerable improvement over the processes hitherto used for manufacturing jasmone inasmuch as yields of jasmone can be obtained which are far beyond the values attainable by the conventional methods. The yields amount to at least 44% of olfactorily pure jasmone, based on 3-hexenyl halide used as an intermediate. Moreover, the new method saves a considerable amount of labour and equipment costs as compared with the conventional methods. The time needed for the manufacture of a given amount of jasmone by the method of the invention is only about one third of the time required in the classical method. A further advantage of the invention consists in the fact that the obtained jasmone has a degree of purity which makes superfluous the complicated and time-consuming purification of the jasmone prepared by the prior art methods.

The method of this invention is not only useful for preparing jasmone but can also be generally applied to the manufacture of numerous isomers and homologs of jasmone.

In carrying out the first step of the new method, viz. the metalation of 2-methyl-furan, there can be used alkali metal derivatives, for example sodium or lithium derivatives of aliphatic, aromatic or mixed aliphatic-aromatic hydrocarbons, preferably hydrocarbons having a lower acidity than 2-methyl-furan. For instance, lower alkylsodium or lower alkyllithium such as methyl- or ethylsodium and methyl- or ethyllithium, phenylsodium or phenyllithium, and benzylsodium or benzyllithium can be used. The lithiumorganic compounds are particularly useful because they are easily accessible. Good results are obtained with n-butyllithium. According to a preferred mode of operation 2-methylfuran is reacted in tetrahydrofuran at temperatures below 0°C., e.g. between −15° and −30°C., with n-butyllithium. The reaction must be carried out in an inert oxygen- and humidity-free atmosphere, e.g. under dry nitrogen or argon. Mixtures of solvents containing tetrahydrofuran and other solvents, e.g. saturated hydrocarbons such as n-hexane, petroleum ether, etc., or ethers such as ethyl ether, isopropyl ether, dioxan, etc., can be used instead of pure tetrahydrofuran as the reaction medium. If mixtures of solvents are used, the reaction between 2-methylfuran and n-butyllithium can be carried out at temperatures above 0°C., e.g. at temperatures as high as 60°C.

In the second step of the new method the metal derivative of 2-methylfuran is reacted with a halide of the formula $R-CH_2-X$ (II), wherein X is a halogen, e.g. chlorine or bromine. Halides which can be used in this step include e.g. 1-bromo-3-butene, 1-bromo-3-pentene, 1-bromo-hexane, 1-bromo-3-hexene, 1-bromo-4-hexane, 1-bromo-5-hexene, 1-bromo-4-methyl-3-pentene, bromo-1-3,5-hexadiene, etc. The reaction can be carried out in a medium consisting of the same solvents as used in the first step. According to a preferred mode of operation the reaction solution obtained in the first step is used directly, and the metal derivative, e.g. the lithium derivative of 2-methylfuran dissolved therein is subjected to the action of the halide at temperatures below 0°C., e.g. at −15° to −30°C., with exclusion of oxygen and humidity. It is possible to operate at higher temperatures, e.g. room temperature or reflux temperature, in those cases where the reaction medium is not pure tetrahydrofuran but consists of the above-mentioned solvent mixtures.

The third step of the method of this invention consists in treating the 2,5-disubstituted furan obtained in the second step so as to open the furan ring. The ring opening can be brought about by heating the 2,5-disubstituted furan in an acidic aqueous medium, e.g. at temperatures between 100° and 150°C. Aqueous solutions of strong inorganic acids, such as $H_2SO_4$, or of acid salts, such as potassium bisulphate, or of strong organic acids, such as p-toluenesulphonic acid, are conveniently used for this purpose. The $p_H$ of the acidic solution can be comprised e.g. between 1 and 2. In order to obtain a homogeneous reaction solution it is advantageous to add to the reaction medium a solubiliser for the 2,5-disubstituted furan. Solubilisers which can be used include e.g. organic acids, such as acetic acid, alcohols, e.g. methanol or ethanol, as well as ethers, e.g. dioxan.

In the last step of the inventive method the dione of formula (III) is cyclised to form the final cyclopentenone derivative. This cyclisation can be brought about by heating the dione in a strongly alkaline aqueous medium, e.g. in an aqueous sodium or potassium hydroxide solution having a $p_H$ of about 13 to 14, e.g. at the reflux temperature of the reaction mixture. In order to obtain a homogeneous reaction solution it is convenient to add a solubiliser for the dione to the cyclisation medium, e.g. an alcohol, such as methanol or ethanol, or an ether, such as dioxan.

When 1-bromo-cis-3-hexene is used as one of the starting materials in the method of the invention, there is obtained as the end product a mixture of cis-jasmone and trans-jasmone in a ratio by weight of about 70 to 80% of the cis-isomer to 20 to 30% of the trans-isomer. These mixtures can be used without further purification as odoriferous products in the manufacture of perfume compositions. If desired, cis-jasmone can be separated from the trans-isomer by fractional distillation of the said mixtures.

The cyclopentenone derivatives which can be prepared by the method of the present invention, and some of which are new compounds, are fragrant substances each of which has quite a distinctive and characteristic odour which differs in kind from the odours of the other members of the series. They are useful as fragrant ingredients in the manufacture of perfume compositions and furthermore constitute valuable starting materials which can serve in the manufacture of other useful organic compounds.

EXAMPLE 1

30 ml. of tetrahydrofuran distilled over Na were introduced into a three-necked flask equipped with a magnetic stirrer, a dropping funnel and a refrigerator. The flask was rinsed with dry nitrogen to remove the air. The introduction of nitrogen was continued throughout the reaction period. 936 mg. (135 millimoles) of finely cut lithium wire were introduced into the flask. To the slurry cooled to 0°C. there were added, with stirring, a few ml. of a solution of 5.84 g. (63 millimoles) of freshly distilled butyl chloride in 25 ml. of tetrahydrofuran in order to initiate the reaction. After the reaction had started, i.e. after about 5 to 10 minutes when the reaction mixture had become turbid, the remainder of the butyl chloride solution was added within 1 hour, while maintaining the cooling bath between −25° and −30°C. The reaction mixture was stirred for a further hour at −25°C. Then 5.18 g. (63 millimoles) of 2-methylfuran distilled over $CaH_2$ were introduced within 15 minutes whereupon the reaction mixture was further stirred for 4 hours at −15°C. Then 10.30 g. (63 millimoles) of 1-bromo-cis-3-hexene diluted with 10 ml. of tetrahydrofuran were added within 20 minutes at −15°C. The reaction mixture was stirred for a further hour at −15°C., then allowed to stand over night at room temperature and finally poured onto crushed ice. The mixture was twice extracted with ether. The ethereal extract was washed twice with water, then twice with saturated NaCl solution, then dried over $Na_2SO_4$ and concentrated. There were obtained 9.8 g. of crude 2-methyl-5-(cis-3-hexenyl)-furan in the form of an oil which was used directly for the next reaction step without any further purification.

A sample of 2-methyl-5-(cis-3-hexenyl)-furan purified by preparative gas chromatography had a refraction index of $n_D^{26} = 1.4671$.

To a solution of 9.8 g. of crude 2-methyl-5-(cis-3-hexenyl)-furan in 10 ml. of glacial acetic acid there were added 5 ml. of water and 0.4 ml. of 20% sulfuric acid whereupon the mixture was stirred for 3 hours at 120°C. (bath temperature) and then poured into water. The mixture was twice extracted with pentane. The extract was washed twice with saturated sodium hydrogen carbonate solution and three times with water, then dried over $Na_2SO_4$ and concentrated. There were obtained 8.4 g. of a dark brown oil which was subjected to a fractional distillation. 4.63 g. of a fraction distilling over at 79°–82°C./0.05 mm. Hg and consisting mainly of cis-8-undecen-2,5-dione were obtained. Yield: 40.5% of the theory, based on 1-bromo-cis-3-hexene.

After purification by redistillation the dione had the following physical properties: B.p. = 65°C./0.02 mm. Hg., $n_D^{26} = 1.4523$.

A mixture of 2.8 g. of cis-8-undecen-2,5-dione, 7 ml. of ethanol and 25 ml. of 0.5 N sodium hydroxide solution was refluxed for 5 hours in a nitrogen atmosphere. The reaction mixture was then cooled and twice extracted with pentane. The extract was washed twice with water, dried over sodium sulfate and concentrated. There remained 2.52 g. of an oil which was subjected to a fractional distillation at a bath temperature of 80°–100°C. and 0.05 mm. Hg in a spinning band column. There was obtained 2.09 g. of jasmone, corresponding to a yield of 83.5% of the theory (based on the dione). Physical properties: $n_D^{26} = 1.4955$; UV spectrum: $\lambda_{max} = 234$ m$\mu$; $\epsilon = 13930$. This product consisted of about 75% by weight of cis-jasmone and of about 25% of trans-jasmone.

The 2,4-dinitrophenyl-hydrazone was obtained in a yield of 81%. After one crystallisation it had an m.p. of 115°–117°C.

The mixture of isomers can be used as such in perfumery. cis-Jasmone can be separated in pure form from the trans-isomer by fractional distillation.

EXAMPLE 2

Into a flask rinsed with argon and equipped with a stirrer, a thermometer, a dropping funnel as well as an inlet and an outlet for argon there were introduced 750 ml. of technical tetrahydrofuran and a solution of 117 g. (1.83 moles) of n-butyllithium in 1 liter of petroleum ether (boiling range: 60°–80°C.). The introduction of a weak current of argon is continued throughout the whole reaction period. The contents of the flask was cooled to −15°C. and there were added thereto within 1 hour, while stirring, 150 g. (1.83 moles) of technical 2-methylfuran. The temperature of the reaction mixture was constantly maintained at −15°C. Stirring was continued for a further 4 hours at −15°C. after the addition of 2-methylfuran was completed. To the reaction mixture there were then slowly added at −15°C. within 2 hours, while stirring, 297 g. (1.83 moles) of 1-bromo-cis-3-hexene. The reaction mixture was then stirred for a further hour at −15°C. and then allowed to stand at room temperature for 2 days. The reaction mixture was subsequently refluxed for 5 hours. Then the reaction mixture was poured into a mixture of 1 liter of water and 500 g. of ice and shaken. The organic phase separated by decanting was washed twice with 100 ml. of water. By evaporation of the petroleum ether under reduced pressure (10 mm. Hg) at a bath temperature of 55°C. there were obtained 256 g. of a product consisting mainly of 2-methyl-5-(cis-3-hexenyl)-furan which was used without any further purification for the next reaction. A sample of 2-methyl-5-(cis-3-hexenyl)-furan purified by gas chromatography had a refraction index of $n_D^{26} = 1.4671$.

A mixture of 256 g. (1.56 moles) of 2-methyl-5-(cis-3-hexenyl)-furan, 260 ml. of glacial acetic acid, 130 ml. of water and 10 ml. of 20% sulfuric acid was heated for 6 hours at an oil bath temperature of 120°C., while vigorously stirring, in a flask equipped with a stirrer, a thermometer and a refrigerator. The reaction mixture was cooled to room temperature and poured into 100 ml. of ice water. The mixture was extracted twice with 100 ml. portions of petroleum ether. The combined petroleum ether extracts were twice washed with 50 ml. portions of 5% sodium hydrogen carbonate solution, then three times with 50 ml. portions of water and finally dried over sodium sulfate. By evaporation of the solvent in vacuo there were obtained 210 g. of crude product which was distilled in a high vacuum in a Vigreux column. There were thus obtained 164.5 g. of cis-8-undecen-2,5-dione of b.p. 66°–70°C./0.01 mm Hg; $n_D^{23}$ = 1.4510. Yield: 49.5% of the theory, based on 1-bromo-3-hexene.

A mixture of 160 g. (0.88 mole) of cis-8-undecen-2,5-dione, 400 ml. of ethanol and 1.43 liters of 0.5 N sodium hydroxide solution was refluxed for 5 hours while stirring vigorously. The reaction mixture was cooled to room temperature and extracted three times with 200 ml. portions of petroleum ether. The combined petroleum ether extracts were washed twice with 100 ml. portions of water and then dried over sodium sulfate. The solvent was evaporated in vacuo. By fractional distillation of the residue in a high vacuum in a Vigreux column there were obtained 125 g. of olfactorily pure jasmone of b.p. 56°–60°C./0.01 mm. Hg; $n_D^{20}$ = 1.4986. This product consisted of 75% of cis-jasmone and of 25% of trans-jasmone. Yield: 43% of the theory based on 2-methylfuran. An additional quantity of olfactorily pure jasmone was obtained by redistilling the combined forerun and tail fractions resulting from the fractional distillation.

The 2,4-dinitrophenyl-hydrazone obtained in a yield of 81% melted at 115°–117°C. after one recrystallisation from ethanol.

The 1-bromo-cis-3-hexene used as starting material in Examples 1 and 2 can be prepared as follows:

5.36 kg. (53.6 moles) of cis-3-hexen-1-ol, 1.19 kg. (15.1 moles) of pyridine distilled over NaOH and 2 liters of petroleum ether (boiling range: 30°–50°C.) were introduced into a 20 liter-flask equipped with a stirrer, a dropping funnel, a thermometer, and a refrigerator provided with a calcium chloride tube. To the solution cooled to −10°C. there were introduced slowly, while stirring, 5.8 kg. (21.5 moles) of phosphorus tribromide. The temperature of the reaction mixture is constantly maintained between 0° and −10°C. When the addition of $PBr_3$ was completed, the reaction mixture was stirred for a further 2 hours without cooling. The petroleum ether was evaporated at normal pressure whereupon the residue was distilled at 10 mm. Hg, and the fraction distilling between 45° and 52°C. was collected. The distillate was washed twice with 1 liter portions of water, once with 500 ml. of 5% sodium hydroxide solution and finally washed neutral with water. After drying over sodium sulfate the liquid was distilled in a Vigreux column in vacuo. There were obtained 5.76 kg. of 1-bromo-cis-3-hexene at 40°–48°C./7 mm. Hg; $n_D^{20}$ = 1.4726. Yield: 66% of the theory.

EXAMPLE 3

By applying the procedure described in Example 1 and using 1.87 g. (0.27 mole) of lithium, 11.7 g. (0.13 mole) of butyl chloride, 10.4 g. (0.13 mole) of 2-methylfuran, 20.6 g. (0.13 mole) of bromo-1-trans-4-hexene and 130 ml. of tetrahydrofuran, there were obtained 10.5 g. of 2-methyl-5-(trans-4-hexenyl)-furan; b.p. = 84°–85°C./11 mm.; $n_D^{20}$ = 1.4702; $d_4^{20}$ = 0.8971.

9.8 g. of this disubstituted furan were reacted with 10 ml. of acetic acid, 5 ml. of $H_2O$ and 0.4 ml. of 20% sulfuric acid in the manner described in Example 1. There were thus obtained 9.73g. of trans-9-undecen-2,5-dione; b.p. = 81°–83°C./0.01 mm.; $n_D^{20}$ = 1.4550; $d_4^{20}$ = 0.9335.

9.0 g. of this dione were reacted with 80 ml. of 0.5 N NaOH in 22.5 ml. of ethanol in the manner described in Example 1. There were thus obtained 7.54 g. of 3-methyl-2-(trans-3-pentenyl)-2-cyclopenten-1-one; b.p. = 70.5°C./0.02 mm; $n_D^{20}$ = 1.4950; $d_4^{20}$ = 0.9430. This product had a lactonic and fruity odour.

EXAMPLE 4

By applying the procedure described in Example 1 and using 4.68 g. of lithium, 29.2 g. of butyl chloride, 25.9 g. of 2-methylfuran, 52.0 g. of 1-bromo-hexane and 325 ml. of tetrahydrofuran, there were obtained 38.7 g. of 2-methyl-5-hexyl-furan; b.p. = 86°C./11 mm.; $n_D^{20}$ = 1.4540; $d_4^{20}$ = 0.8736.

41.3 g. of this disubstituted furan were reacted with 42 ml. glacial acetic acid, 21 ml. of water and 1.7 ml. of 20% sulfuric acid in the manner described in Example 1. There were thus obtained 34.5 g. of undecan-2,5-dione; b.p. = 78°C./0.015 mm.

23.3 g. of this dione were treated with 210 ml. of 0.5 N NaOH and 60 ml. of ethanol in the manner described in Example 1. There were thus obtained 19.1 g. of 3-methyl-2-hexyl-2-penten-1-one (dihydrojasmone); b.p. = 56°C./0.001 mm.; $n_D^{20}$ = 1.4793; $d_4^{20}$ = 0.9157.

EXAMPLE 5

By applying the procedure described in Example 1 and using 15 g. of lithium, 93.5 g. of butyl chloride, 82.5 g. of 2-methylfuran, 165g. of 14-methyl-3-pentene and 1040 ml. of tetrahydrofuran, there were obtained 73.0 g. of 2-methyl-5-(3-pentenyl)-furan; b.p. = 80°C./11 mm.; $n_D^{20}$ = 1.4741; $d_4^{20}$ = 0.9109.

68 g. of this disubstituted furan were reacted with 70 ml. of glacial acetic acid, 35 ml. of water and 2.7 ml. of 20% sulfuric acid in the manner described in Example 1. There were thus obtained 27.2 g. of 4-methyl-8-decen-2,5-dione; b.p. = 72°C./0.001 mm.; $n_D^{20}$ = 1.4626; $d_4^{20}$ = 0.9507.

32.4 g. of this dione were treated with 230 ml. of 0.5 N NaOH and 70 ml. of ethanol in the manner described in Example 1. There were thus obtained 27.4 g. of 3-methyl-2-(3-methyl-2-butenyl)-2-penten-1-one; b.p. = 80°C./0.04 mm.; $n_D^{20}$ = 1.5029; $d_4^{20}$ = 0.9483. This compound has not been described in the literature.

EXAMPLE 6

By applying the procedure described in Example 1 and using 6.0 g. of lithium, 37.3 g. of butyl chloride, 33.2 g. of 2-methylfuran, 54.3 g. of 1-bromo-3-butene and 415 ml. of tetrahydrofuran, there were obtained 12.36 g. of 2-methyl-5-(3-butenyl)-furan; b.p. = 52°C./11 mm.; $n_D^{20}$ = 1.4609; $d_4^{20}$ = 0.9075.

11.5 g. of this disubstituted furan were reacted with 13.3 ml. of acetic acid, 6.65 ml. of water and 0.54 ml. of 20% sulfuric acid. There were thus obtained 9.61 g. of 8-nonen-2,5-dione; b.p. = 67°C./0.04 mm.; $n_D^{20}$ = 1.4496; $d_4^{20}$ = 0.9538.

9.12 g. of this dione were treated with 95 ml. of 0.5 N NaOH and 28 ml. of ethanol in the manner described in Example 1. There were thus obtained 6.98 g. of 3-methyl-2-(2-propenyl)-2-cyclopenten-1-one; b.p. = 98°C./11 mm.; $n_D^{20}$ = 1.4992; $d_4^{20}$ = 0.9569. This product has a fonugreek-lovage-like odour.

EXAMPLE 7

By applying the procedure described in Example 1 and using 2.7 g. of lithium, 16.65 g. of butyl chloride, 15.0 g. of 2-methylfuran, 27 g. of 1-bromo-trans-3-pentene and 210 g. of tetrahydrofuran, there were obtained 13.4 g. of 2-methyl-5-(3-pentenyl)-furan; b.p. = 69°C./11 mm.; $n_D^{20}$ = 1.5014; $d_4^{20}$ = 0.9518.

8.7 g. of this disubstituted furan were reacted with 9.6 ml. of acetic acid, 4.8 ml. of water and 0.4 ml. of 20% sulfuric acid in the manner described in Example 1. There were thus obtained 7.99 g. of 8-docen-2,5-dione; b.p. = 70°C./0.005 mm.; $n_D^{20}$ = 1.4538; $d_4^{20}$ = 0.9446.

7.5 g. of this dione were treated with 72 ml. of 0.5 N NaOH and 21 ml. of ethanol in the manner described in Example 1. There were thus obtained 6.13 g. of 3-methyl-2-(trans-2-butenyl)-2-cyclopenten-1-one; b.p. = 58°C./0.01 mm.; $n_D^{20}$ = 1.4704; $d_4^{20}$ = 0.9052. This compound which has not been described in the literature has a mushroomlike odour.

EXAMPLE 8

By applying the procedure described in Example 1 and using 3.68 g. of lithium, 22.2 g. of butyl chloride, 19.7 g. of 2-methylfuran, 39.2 g. of 1-bromo-5-hexone and 260 g. of tetrahydrofuran, there are obtained 22.0 g. of 2-methyl-5-(5-hexenyl)-furan; $n_D^{20}$ = 1.476.

12.4 g. of this disubstituted furan were reacted with 12.0 ml. of acetic acid, 6.0 ml. of water and 0.5 ml. 20% sulfuric acid. There were thus obtained 10.3 g. of 10-undecen-2,5-dione; $n_D^{20}$ = 1.458.

5.1 g. of this dione were treated with 50 ml. of 0.5 N NaOH and 14 ml. of ethanol in the manner described in Example 1. There were thus obtained 4.0 g. of 3-methyl-2-(4-pentenyl)-2-cyclopenten-1-one; $n_D^{20}$ = 1.497.

EXAMPLE 9

By applying the procedure in Example 1 and using 6.9 g. of lithium, 42.5 g. of butyl chloride, 37.8 g. of 2-methylfuran, 74.0 g. of 1-bromo-trans-3,5-hexadiene and 500 ml. of tetrahydrofuran, there were obtained 33.5 g. of 2-methyl-5-(trans-3,5-hexadienyl)-furan; $n_D^{20}$ = 1.503.

18.7 g. of this disubstituted furan were reacted with 20.0 ml. of acetic acid, 10.0 ml. of water and 0.8 ml. of 20% sulfuric acid. There were thus obtained 14.3 g. of 8,10-undecadien-2,5-dione; $n_D^{20}$ = 1.491.

11.7 g. of this dione were treated with 110 ml. of 0.5 N NaOH and 30 ml. of ethanol in the manner described in Example 1. There were thus obtained 9.3 g. of 3-methyl-2-(trans-2,4-pentadienyl)-2-cyclopenten-1-one; $n_D^{20}$ = 1.520.

The preceding Examples are given by way of illustration only and should not be construed as a limitation of the invention.

What we claim is:

1. A process for the preparation of a dione of the formula

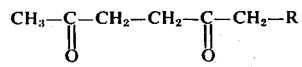

wherein R represents a member selected from the group consisting of —CH$_2$—CH=CH$_2$, —CH$_2$—CH=CH—CH$_3$,

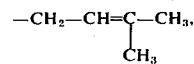

—CH$_2$—CH=CH—CH$_2$—CH$_3$, —CH$_2$—CH$_2$—CH=CH—CH$_3$, —CH$_2$—CH$_2$—CH$_2$—CH=CH$_2$ and —CH$_2$—CH=CH—CH=CH$_2$ which comprises a. metallating 2-methylfuran in the 5-position by an interchange reaction with an alkali metal-organic compound selected from the group consisting of lower alkyl sodium, lower alkyl lithium, phenyl sodium, phenyl lithium, benzyl sodium and benzyl lithium, said step being conducted in an inert atmosphere and in an organic solvent medium at a temperature of from about 60°C to about −30°C;

b. condensing the resulting metal derivative of 2-methylfuran in an organic solvent medium, in an inert atmosphere and at a temperature of from the reflux temperature of the solvent to about −30°C with a halide of the formula

wherein R has the previously indicated significance in order to form a 2,5-disubstituted furan of the formula

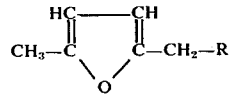

and, c. treating the disubstituted furan at a temperature of from about 100° to about 150°C with an aqueous acid selected from the group consisting of mineral acids and strong organic acids to cause the opening of the furan ring.

2. The method according to claim 1 wherein 1-bromo-3-butene is used as a starting compound.

3. The method according to claim 1 wherein 1-bromo-3-pentene is used as a starting compound.

4. The method according to claim 1 wherein 1-bromo-4-methyl-3-pentene is used as a starting compound.

5. The method according to claim 1 wherein 1-bromo-cis-3-hexene is used as a starting compound.

6. The method according to claim 1 wherein 1-bromo-4-hexene is used as a starting compound.

7. The method according to claim 1 wherein 1-bromo-5-hexene is used as a starting compound.

8. The method according to claim 1 wherein 1-bromo-3,5-hexadiene is used as a starting compound.

* * * * *